(12) United States Patent
Sato et al.

(10) Patent No.: US 10,392,335 B2
(45) Date of Patent: Aug. 27, 2019

(54) METHOD FOR PRODUCING HYDROXYPIVALALDEHYDE

(71) Applicant: Mitsubishi Gas Chemical Company, Inc., Chiyoda-ku (JP)

(72) Inventors: Yumi Sato, Kurashiki (JP); Masahiro Yamane, Kurashiki (JP)

(73) Assignee: Mitsubishi Gas Chemical Company, Inc., Chiyoda-ku (JP)

( * ) Notice: Subject to any disclaimer, the term of this patent is extended or adjusted under 35 U.S.C. 154(b) by 0 days.

(21) Appl. No.: 16/068,259

(22) PCT Filed: Jan. 5, 2017

(86) PCT No.: PCT/JP2017/000171
§ 371 (c)(1),
(2) Date: Jul. 5, 2018

(87) PCT Pub. No.: WO2017/119458
PCT Pub. Date: Jul. 13, 2017

(65) Prior Publication Data
US 2019/0023638 A1    Jan. 24, 2019

(30) Foreign Application Priority Data
Jan. 7, 2016   (JP) ................................ 2016-001698

(51) Int. Cl.
*C07C 45/75*   (2006.01)
*C07C 47/00*   (2006.01)
*C07C 47/56*   (2006.01)
*C07C 45/72*   (2006.01)
*C07C 45/80*   (2006.01)
*C07C 47/19*   (2006.01)
*C07C 47/198*  (2006.01)
*C07C 45/83*   (2006.01)

(52) U.S. Cl.
CPC .............. *C07C 47/56* (2013.01); *C07C 45/72* (2013.01); *C07C 45/75* (2013.01); *C07C 45/80* (2013.01); *C07C 45/83* (2013.01); *C07C 47/19* (2013.01); *C07C 47/198* (2013.01)

(58) Field of Classification Search
CPC ......... C07C 45/83; C07C 45/75; C07C 47/56; C07C 47/19
See application file for complete search history.

(56) References Cited

U.S. PATENT DOCUMENTS

| | | | |
|---|---|---|---|
| 4,036,888 | A | 7/1977 | Couderc et al. |
| 4,250,337 | A | 2/1981 | zur Hausen et al. |
| 6,201,159 | B1 | 3/2001 | Choi et al. |
| 2010/0113836 | A1 | 5/2010 | Sirch et al. |
| 2011/0184212 | A1 | 7/2011 | Schulz et al. |

FOREIGN PATENT DOCUMENTS

| | | |
|---|---|---|
| GB | 1 353 761 A | 5/1974 |
| JP | 47-6967 A | 4/1972 |
| JP | 48-39420 A | 6/1973 |
| JP | 51-68514 A | 6/1976 |
| JP | 55-4396 A | 1/1980 |
| JP | 63-135347 A | 6/1988 |
| JP | 7-82192 A | 3/1995 |
| JP | 2001-302673 A | 10/2001 |
| JP | 3224547 B2 | 10/2001 |
| JP | 2007-70339 A | 3/2007 |
| JP | 2010-520250 A | 6/2010 |
| JP | 2011-527993 A | 11/2011 |

OTHER PUBLICATIONS

International Search Report dated Feb. 21, 2017. in PCT/JP2017/000171 filed Jan. 5, 2017.
Margheri, G. et al., "Oligomerization of aldehydes catalyzed by cobalt carbonyl", Journal of Molecular Catalysis A: Chemical, vol. 132, 1998, pp. 189-201.
Rosinger, H., "Uber Kondensationsprodukte von Glyoxal und isobutyraldehyd", vol. 28, 1908, pp. 947-960.

*Primary Examiner* — Sikarl A Witherspoon
(74) *Attorney, Agent, or Firm* — Oblon, McClelland, Maier & Neustadt, L.L.P.

(57) ABSTRACT

There is provided a method for producing hydroxypivalaldehyde (HPA), including steps (i) to (iii) below in this order, Step (i): a reaction step of reacting IBAL with FA to produce a reaction solution containing HPA, step (ii): an extraction step of extracting the reaction solution with an aldehyde solvent represented by formula (1) under basicity to obtain an extract containing HPA, and step (iii): a distillation and collection step of distilling the extract and then collecting HPA from the residue,

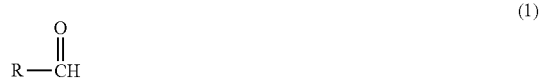

(1)

wherein R represents a saturated alkyl group having 3 or more and 7 or less carbon atoms, further wherein the distillation step of the step (iii) is a step of distilling an extract in the presence of water, and an amount of the water which is subjected to the distillation is 100 parts by mass or more and 2,000 parts by mass or less with respect to a total amount, 100 parts by mass, of isobutyraldehyde (IBAL) derived from a raw material and an aldehyde solvent represented by formula (1) in an extract which is subjected to the distillation.

The method enables HPA to be mass-produced and the collecting ratio of HPA to be improved while selectively removing impurities other than water contained in HPA, specifically IBAL and the like. According to the method for producing HPA as mentioned above, it is possible to reduce the content of neopentyl glycol-isobutyrate, isobutylaldehyde-hydroxypivalaldehyde-acetal, and isobutylaldehyde-hydroxypivalaldehyde-aldol as specific impurities byproduced from HPA.

12 Claims, No Drawings

METHOD FOR PRODUCING HYDROXYPIVALALDEHYDE

TECHNICAL FIELD

The present invention relates to a method for producing hydroxypivalaldehyde.

BACKGROUND ART

Hydroxypivalaldehyde (hereinbelow, HPA) is a raw material for neopentyl glycol (hereinbelow, NPG). HPA is also used as a raw material for acetal compounds such as spiroglycol (hereinbelow, SPG). When HPA is subjected to hydrogenation reaction (hereinbelow, hydrogenation), for example, NPG is obtained. From HPA and a polyhydric alcohol, an acetal compound such as SPG is obtained. MPG is used as a raw material for alkyd resin paints, polyester resins, and powdered paints. SPG is used as an antioxidant and also as a raw material for highly heat resistant resin.

HPA is generally obtained by an aldol reaction of isobutyraldehyde (hereinbelow, IBAL) with formaldehyde (hereinbelow, FA) under basic conditions. In this case, HPA contains, as impurities, NPG, FA, a catalyst used in the reaction, and a carboxylate salt such as formate salt which is produced as byproduct, as described in Patent Literature 1 and the like. As described in Patent Literature 1 and the like, it is known that these impurities inhibit hydrogenation when NPG is produced.

In Patent Literature 2, it is mentioned that impurity of aldehydes such as IBAL and FA, which are contained in HPA when SPG is produced, influences the quality of SPG. Thus, purification for obtaining highly pure HPA is required.

As methods of removing impurities contained in HPA, crystallization, extraction, and distillation have been reported. For example, in Patent Literature 1, a process of purifying HPA by crystallization is described. By this method, HPA having the purity more than 98% by mass can be obtained. In Patent Literature 3, in order to remove carboxylate salts contained in the reaction liquid after HPA is synthesized, an operation similar to extraction is carried out. Water is added to the reaction liquid, which is cooled and then allowed to separate into two layers. Carboxylate salts are removed by partitioning HPA into the oil layer and the carboxylate salts into the water layer.

In Patent Literature 4, a process of removing low-boiling-point impurities by distillation is described. Additionally, as a method including extraction and distillation in combination, a process in which extraction by octanol is carried out to remove organic acid salt and then low-boiling-point impurities are removed by distillation is described in Patent Literature 5.

CITATION LIST

Patent Literature

Patent Literature 1: Japanese Unexamined Patent Application Publication No. 2007-70333
Patent Literature 2: Japanese Unexamined Patent Application Publication No. 2001-302673
Patent Literature 3: Japanese Unexamined Patent Application Publication No. Hei07-082192
Patent Literature 4: Japanese Unexamined Patent Application Publication (Translation of PCT Application) No. 2010-520250
Patent Literature 5: Japanese Patent No. 3224547

SUMMARY OF INVENTION

Technical Problem

HPA, which is used as a raw material for NPG and SPG, is, together with water, subjected to reaction, as described in Patent Literature 2 and Patent Literature 3. Meanwhile, impurities other than water contained in HPA inhibit the reaction and influence the quality of the target product. Thus, the impurities other than water contained in HPA have to be reduced.

It should be noted that HPA, in the absence of water, is partly converted into neopentyl glycol-hydroxypivalate by a secondary reaction. Also when HPA as a raw material for NPG and SPG is subjected to a reaction, an operation of dissolving and adding HPA is carried out. If heat is applied, HPA is more likely to be degraded into neopentyl glycol-hydroxypivalate eater. Thus, water should be allowed to coexist in order to reduce the temperature on dissolution. Particularly, synthesis of SPG or the like is carried out in an aqueous solvent, and thus, presence of water has no influence. As mentioned above, presence of water as an impurity causes no problem.

The yield from the crystallization described in Patent Literature 1 is at most 84%, and the productivity of high purity HPA has an issue. Furthermore, crystallization purification is not suitable for mass production due to high costs for construction and operation of an apparatus. Crystallization that uses water as the solvent results in a large amount of waste water. Accordingly, treatment of the waste water described above is also required, and crystallization is not preferable from the viewpoint of environment and additionally economic efficiency.

The extraction described in Patent Literature 3 can remove carboxylate salts such as formate salts, but removal of FA, NPG, and other impurities is insufficient. With respect to HPA, 0.32% by mass of FA still remains.

The distillation described in Patent Literature 4 can remove unreacted IBAL and triethylamine used as the catalyst. However, it is impossible to remove impurities that have formed salts such as formate salts and compounds susceptible to thermal denaturation such as FA. The distillation, which is a process of removing only low-boiling point impurities, cannot remove impurities having a boiling point higher than that of HPA.

The combination of removal by extraction and distillation of low-boiling point impurities described in Patent Literature 5 was effective for removal of formate salts and low-boiling point impurities, but 1.74% by mass of IBAL remains with respect to HPA even after the distillation step. Moreover, the combination has problems such as the amount of water of 35% by mass or less with respect to the total of the extraction solvent and IBAL as the raw material, the high content of neopentyl glycol ester even after distillation, and much residual IBAL even after distillation.

As mentioned above, none of methods known so far has been able to obtain HPA at a high yield while selectively removing impurities other than water contained in HPA, specifically IBAL and the like. Particularly, it has been difficult for conventional techniques to sufficiently reduce IBAL from HPA.

Accordingly, it is an object of the present invention to provide a method for producing HPA obtained from IBAL and FA, wherein the method enables HPA to be mass-produced and the collecting ratio of HPA to be improved while selectively removing impurities other than water contained in HPA, specifically IBAL and the like.

Additionally, it is another object of the present invention to provide a method for producing HPA, wherein specific impurities secondarily produced as byproduct from HPA, such as neopentyl glycol-isobutyrate, isobutyraldehyde-hydroxypivalaldehyde-acetal, and isobutyraldehyde-hydroxypivalaldehyde-aldol forms are specified to be contained at a low level.

Solution to Problem

The present inventors have intensively studied to solve the above problems. As a result, the present inventors have found formate salts contained in HPA can be partitioned into the water layer by extracting HPA reaction liquid under basic conditions with an aldehyde solvent such as IBAL. The present inventors additionally have found that FA also can be reduced.

Furthermore, the present inventors have found that thereafter, when other low-boiling point impurities are removed together with the extraction solvent by distillation, water is allowed to coexist to thereby obtain highly pure HPA, from which impurities other than water have been selectively removed, at a high yield, thereby having completed the present invention.

That is, the present invention relates to following <1> to <12>.
<1>
A method for producing hydroxypivalaldehyde comprising steps (i) to (iii) below in this order, step (i): a reaction step of reacting isobutyraldehyde with formaldehyde to obtain a reaction solution containing hydroxypivalaldehyde, step (ii): an extraction step of extracting the reaction solution with an aldehyde solvent represented by formula (1) under basicity to obtain an extract containing hydroxypivalaldehyde, and step (iii): a distillation and collection step of distilling the extract and then collecting hydroxypivalaldehyde from a still residue,

wherein R represents a saturated alkyl group having 3 or more and 7 or less carbon atoms, further wherein the distillation step of the step (iii) is a step of distilling the extract in the presence of water, and an amount of the water which is subjected to the distillation is 100 parts by mass or more and 2,000 parts by mass or less with respect to a total amount, 100 parts by mass, of isobutyraldehyde derived from a raw material and an aldehyde solvent represented by formula (1) in the extract which is subjected to the distillation.
<2>
The method for producing hydroxypivalaldehyde according to <1>, wherein the amount of the water which is subjected to the distillation is 50 parts by mass or more and 1,000 parts by mass or less with respect to 100 parts by mass of hydroxypivalaldehyde in the extract which is subjected to the distillation.

<3>
The method for producing hydroxypivalaldehyde according to <1>, comprising a step of concentrating the extract after the step (ii) and before the step (iii).

The method for producing hydroxypivalaldehyde according to any of <1> to <3>, wherein the aldehyde solvent represented by formula (1) is isobutyraldehyde.
<5>
The method for producing hydroxypivalaldehyde according to any of <1> to <4>, wherein the step (iii) is a step of continuously supplying the extract and water, while being mixed, to a distillation apparatus and collecting hydroxypivalaldehyde from the still residue.
<6>
The method for producing hydroxypivalaldehyde according to any of <1> to <5>, wherein the step (iii) is a step of continuously supplying the extract and water, while being mixed and heated, to a distillation apparatus and collecting hydroxypivalaldehyde from the still residue.
<7>
The method for producing hydroxypivalaldehyde according to any of <1> to <6>, comprising, after the step (iii), a distilling-out and collection step of further distilling the still residue and collecting hydroxypivalaldehyde as a fraction.
<8>
The method for producing hydroxypivalaldehyde according to any of <1> to <7>, comprising, after the step (iii), a step of controlling the content of at least one compound selected from the group consisting of compounds represented by following formulas (2) to (4):

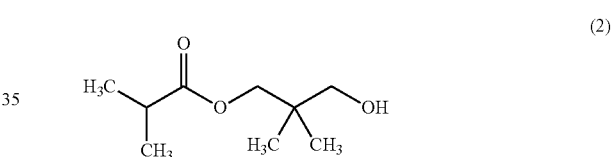

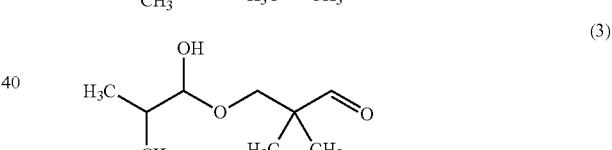

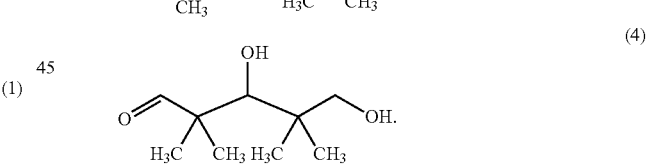

<9>
The method for producing hydroxypivalaldehyde according to any of <1> to <8>, comprising, after the step (iii), a step of controlling the content of a compound represented by following compound represented by formula (2):

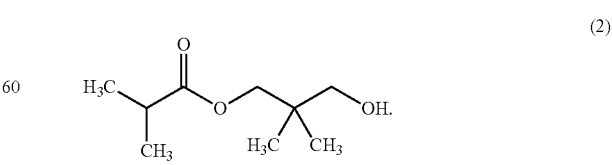

<10>
A compound represented by following formula (3) or following formula (4):

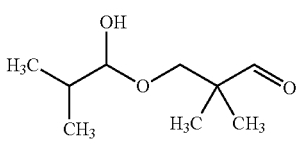

(3)

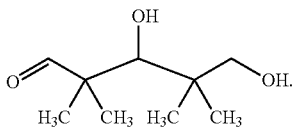

(4)

<11>
A method for producing a compound represented by formula (3), comprising a step of reacting isobutyraldehyde with hydroxypivalaldehyde;

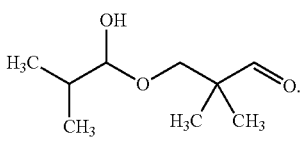

(3)

<12>
A method for producing a compound represented by formula (4), comprising a step of reacting isobutyraldehyde with hydroxypivalaldehyde:

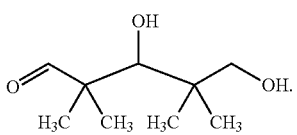

(4)

Advantageous Effects of Invention

According to the present invention, a method for producing HPA obtained from IBAL and FA can be provided, wherein the method enables HPA to be mass-produced and the collecting ratio of HPA to be improved while selectively removing impurities other than water contained in HPA, specifically IBAL and the like. Furthermore, according to the present invention, a method for producing HPA is provided, wherein the content of specific impurities is reduced.

DESCRIPTION OF EMBODIMENT

Hereinbelow, an embodiment of the present invention (hereinbelow, referred to as "the present embodiment") will be described in detail. However, the present invention is not intended to be limited thereto and various modifications can be made without departing from the scope of the invention.

In the present embodiment, the description "A to B" representing the numerical limitation means a numerical range including end points A and B. A<B means A or more and B or less, and A>B means A or less and B or more.

Part(s) by mass and % by mass have the same meaning as part(s) by weight and % by weight, respectively.

Furthermore, in the present embodiment, a combination of preferred aspects is a more preferred aspect.

[Method for Producing Hydroxypivalaldehyde]

A method for producing hydroxypivalaldehyde (HPA) of the present embodiment is a method comprising steps (i) to (iii) below in this order, step (i): a reaction step of reacting isobutyraldehyde (IBAL) with formaldehyde (FA) to obtain a reaction solution containing hydroxypivalaldehyde (HPA), step (ii): an extraction step of extracting the reaction solution with an aldehyde solvent represented by formula (1) under basicity to obtain an extract containing hydroxypivalaldehyde (HPA), and step (iii): a distillation and collection step of distilling the extract and then collecting hydroxypivalaldehyde (HPA) from a still residue,

(1)

wherein R represents a saturated alkyl group having 3 or more and 7 or less carbon atoms, further wherein the distillation step of the step (iii) is a step of distilling the extract in the presence of water, and an amount of the water which is subjected to the distillation is 100 parts by mass or more and 2,000 parts by mass or less with respect to a total amount, 100 parts by mass, of isobutyraldehyde (IBAL) derived from the raw material and an aldehyde solvent represented by formula (1) in the extract which is subjected to the distillation.

The present embodiment is a method for producing HPA, wherein the collecting ratio of HPA is excellent when IBAL is allowed to react with FA in the presence of a basic catalyst to synthesize HPA, and the amount of specific impurities other than water is reduced. After HPA is synthesized, extraction is carried out under basicity using a specific aldehyde solvent represented by the above formula (1) (hereinbelow, also referred to as a specific aldehyde solvent) to extract HPA. Subsequently, IBAL and the specific aldehyde solvent are distilled off from the extract containing HPA by distillation in the presence of water to thereby obtain HPA at a high collecting ratio.

In the present embodiment, although a detailed mechanism of providing a method for producing HPA of which the collecting ratio is excellent and in which the specific impurities are reduced is unknown, a part of the mechanism is presumed as follows.

First, formate salt contained in the HPA reaction liquid (the HPA reaction liquid herein means a reaction liquid after HPA is synthesized from IBAL and FA) can be partitioned into the water layer by extracting and purifying the HPA reaction liquid with a specific aldehyde solvent such as IBAL and water under basic conditions. The extraction also can reduce the content of FA in the HPA reaction liquid.

Thereafter, when other low-boiling point impurities are removed together with the extraction solvent by distillation, there occurs a problem in that IBAL and the specific aldehyde solvent or the extraction solvent inevitably remain in HPA after distillation.

As a result of an investigation on the factor that allows the aldehyde to remain by the present inventors, when HPA is extracted into a specific aldehyde solvent such as IBAL, it has been found that an equilibrium reaction allows a portion of HPA to form secondary products (an example of the structure are shown in formula (2')) of the specific aldehyde solvent and IBAL.

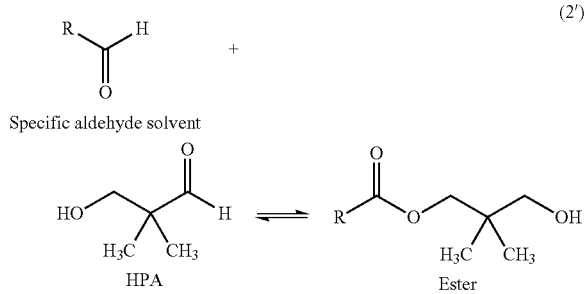

Specific aldehyde solvent / HPA / Ester wherein R represents a saturated alkyl group having 3 or more and 7 or less carbon atoms.

Particularly when IBAL is used as the extraction solvent, it has been found the following reaction occurs.

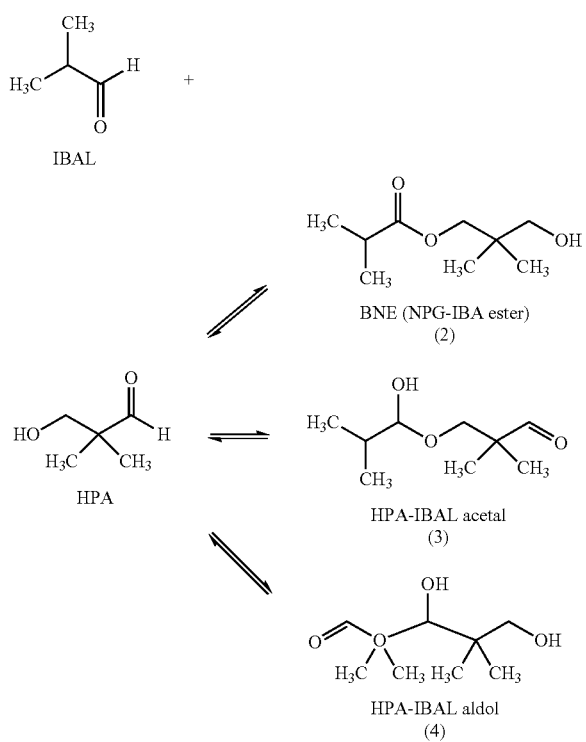

IBAL
BNE (NPG-IBA ester) (2)
HPA
HPA-IBAL acetal (3)
HPA-IBAL aldol (4)

When IBAL as the raw material and the specific aldehyde solvent as the extraction solvent are removed to outside the system, these secondary products regenerate IBAL and the specific aldehyde solvent due to the shift of the equilibrium. Accordingly, if IBAL or the specific aldehyde solvent is distilled off by distillation or the like, IBAL and the specific aldehyde solvent are produced again in HPA.

In the production method of the present embodiment, when the extraction solvent and low-boiling point impurities are distilled off by distillation, the extract is distilled in the presence of water. This distillation decomposes the secondary products described above, removes IBAL and the specific aldehyde solvent incorporated in secondary products to outside the distillation system, and additionally, regenerates HPA from the secondary products. Accordingly, IBAL and aldehydes such as the specific aldehyde solvent can be sufficiently reduced, and the collecting ratio of HPA can be improved. Thus, in the method for producing HPA of the present embodiment, the amount of the specific secondary products is reduced, and highly pure HPA can be obtained at a high yield.

The present embodiment also relates to the novel secondary products described above. Limiting the content of these secondary products enables highly pure HPA to be produced, and the secondary products are useful materials for manufacturing control of HPA. When the content of the impurities in the composition of HPA collected after azeotroped with water is smaller than a control value, degradation in the quality caused by an aldehyde derived by decomposition from impurities can be negligible. When the composition is used as a raw material to synthesize NPG or SPG, the amount of impurities to be produced due to the derived aldehyde can be reduced as much as possible.

<Step (i); Reaction Step>

In the step (i), IBAL is allowed to react with FA to obtain a reaction liquid containing HPA.

For HPA, IBAL and FA, inexpensive raw materials, are preferably subjected to an aldol reaction in the presence of a basic catalyst.

The form of FA used for producing HPA is not particularly limited, and examples thereof include trioxane, paraformaldehyde, or a formaldehyde aqueous solution (formalin). Of these, formalin is preferred. Trioxane, paraformaldehyde, and the formaldehyde aqueous solution (formalin) can be used in admixture as appropriate. A reaction of IBAL with FA is likely to be influenced by the water concentration of the reaction system. When the concentration of IBAL and FA is low, the reaction rate becomes slow, and thus, the concentration of FA is preferably high. When formalin is used as a raw material, the concentration of formalin is preferably 37% by mass or more. The concentration of formalin is preferably 90% by mass or less, more preferably 70% by mass or less.

Examples of the basic catalyst include inorganic bases and organic bases. Examples of the inorganic base include sodium hydroxide, potassium hydroxide, sodium carbonate, and potassium carbonate. Examples of the organic base include amine catalysts such as tertiary amines. In the reaction step, when the basicity becomes extremely high, HPA simultaneously causes a Cannizzaro reaction with unreacted FA to thereby reduce the yield of HPA. In contrast, when the basicity is extremely low, the reaction becomes slow. Thus, an amine catalyst is preferably used, and a tertiary amine is more preferred.

Examples of the tertiary amine include trimethylamine, triethylamine, tripropylamine, triisopropylamine, tributylamine, triisobutylamine, N-methylpiperidine, N-ethylpiperidine, N-methylmorpholine, N-ethylmorpholine, N-methylpyrrolidine, and N-ethylpyrrolidine. Of these, trimethylamine and triethylamine are preferred, and triethylamine is more preferred, from the viewpoint of inexpensive availability.

The content of the basic catalyst can be varied as appropriate depending on the kind. For example, when triethylaniine is used, the molar equivalent of triethylamine is preferably 0.001 to 0.5, more preferably 0.01 to 0.2 with respect to IBAL The aldol reaction of IBAL with FA may be either of batch-type or continuous type. The reaction is also carried out under normal pressure under airtight or in a stream of nitrogen gas.

The molar equivalent of IBAL fed with respect to FA is preferably 0.95 to 1.30, more preferably 0.98 to 1.10.

The reaction temperature is preferably 40 to 98° C., more preferably 80 to 95° C. under normal pressure.

<Step (ii): Extraction Step>

The step (ii) is a step of extracting the reaction liquid obtained in the step (i) (HPA reaction liquid) with an aldehyde solvent represented by following formula (1) (specific aldehyde solvent) under basicity to allow residual formaldehyde to be partitioned into the specific aldehyde solvent as well as to obtain an extract containing HPA (oil layer) (hereinbelow, also referred to as extraction step).

In the extraction step, HPA is collected from the HPA reaction liquid while formate salt and FA are reduced.

(1)

wherein R represents a saturated alkyl group having 3 or more and 7 or less carbon atoms.

In formula (1), R is a saturated alkyl group having 3 or more and 7 or less carbon atoms. R has preferably 3 to 6 carbon atoms, more preferably 3 to 5 carbon atoms, still more preferably 3 or 4 carbon atoms, even still more preferably 4 carbon atoms. When the saturated alkyl group has 3 or more carbon atoms, the miscibility between the aldehyde solvent represented by formula (1) and water is low, and thus liquid separation after extraction can be carried out quickly. When the saturated alkyl group has 7 or less carbon atoms, the aldehyde solvent represented by formula (1) has a boiling point lower than that of the target product, and thus collection of the aldehyde solvent by distillation and reuse thereof are enabled. The saturated alkyl group may be a linear chain or branched chain.

Examples of the specific aldehyde solvent include n-butylaldehyde, isobutyraldehyde (IBAL), n-pentylaldehyde, pivalaldehyde, n-hexylaldehyde, cyclohexanecarboxaldehyde, n-heptylaldehyde, and n-octylaldehyde, Of these, aldehydes of which alkyl group has 3 to 4 carbon atoms are preferred as the specific aldehyde solvent because the effect of reducing impurities is high and the collecting ratio of HPA is high. Furthermore, as the specific aldehyde solvent, because of easy separation from HPA by distillation, n-butylaldehyde and isobutyraldehyde (IBAL) are more preferred, isobutyraldehyde (IBAL) is still more preferred.

One specific aldehyde solvent of the extraction solvent may be used singly or two or more specific aldehyde solvents may be used in admixture.

The specific aldehyde solvent is usually used in an amount of 0.5 to 4 times by mass with respect to the HPA reaction liquid, although the amount depends on the compound used and conditions. When the amount of 0.5 times by mass or more is used with respect to the HPA reaction liquid, loss of HPA into the water layer tends to be reduced. When the amount of 4.0 times by mass or less is used with respect to the HPA reaction liquid, the extraction solvent tends to be easily collected by distillation. A more preferred amount of the extraction solvent used is 0.5 to 3 times by mass, and a still more preferred amount of the extraction solvent used is 0.8 to 2.5 times by mass.

In the extraction step, a solvent other than the specific aldehyde solvent may be concurrently used as an extraction solvent (oil layer) to provide a mixed solvent. When the extraction solvent is a mixed solvent, the content of the specific aldehyde solvent is preferably 50% by mass or more, more preferably 70% by mass or more, still more preferably 90% by mass or more, even still more preferably 95% by mass or more. It is yet even still more preferred to use the specific aldehyde solvent singly.

In the extraction step, water is preferably added together with the specific aldehyde solvent described above, to the HPA reaction liquid. Examples of the water include ion exchange water and pure water. The water is preferably one having a low content of impurities, more preferably pure water. The amount of water to be added is preferably 0.15 to 3 times by mass, more preferably 0.3 to 2 times by mass, still more preferably 0.5 to 1 time(s) by mass with respect to the HPA reaction liquid.

The extraction operation is carried out under basic condition. As a basic index for extraction, the pH of the HPA reaction liquid is preferably in the range of 7.5 to 13.5. When the pH is 13.5 or less, it is possible to inhibit HPA reduction due to progress of a side reaction such as a Cannizzaro reaction. When the pH is 7.5 or more, basicity is sufficient for promoting the reaction between formaldehyde and the extraction solvent. The pH during extraction is more preferably 8.0 to 13.0, still more preferably 8.0 to 11.0.

HPA is usually obtained by an aldol reaction between IBAL and FA in the presence of a basic catalyst, and thus the catalyst used for synthesis can be used as the base during extraction if the pH during extraction is in a preferred range. For adjusting the pH, a basic substance may be added as appropriate.

The base to be newly added may be the same as the catalyst used for HPA synthesis, or a different basic compound may be used. Thus, examples of the basic compound that can be used for adjusting the basicity include inorganic bases such as sodium hydroxide, potassium hydroxide, sodium carbonate, and potassium carbonate and organic bases such as tertiary amines and pyridine. Examples of the tertiary amine include trimethylamine, triethylamine, tripropylamine, triisopropylamine, tributylamine, triisobutylamine, N-methylpiperidine, N-ethylpiperidine, methylmorpholine, N-ethylmorpholine, N-methylpyrrplidine, and N-ethylpyrrolidine. For convenient purification and quality control, as the basic compound that can be used for adjusting the basicity, it is preferred to use the same compound used during synthesis of HPA.

The temperature during extraction is preferably 0 to 70° C. When the temperature is 0° C. or more, extraction can be carried out without solidification of the water layer in the extraction step. When the temperature is 70° C. or less, it is possible to inhibit progress of the side reaction. The temperature during extraction is more preferably 5 to 65° C., still more preferably 15 to 65° C.

The apparatus used for the extraction operation is not particularly limited. It is preferred to select an apparatus having satisfactory stirring efficiency as appropriate depending on the extraction solvent to be used and the temperature during extraction. Examples of the apparatus used in the extraction operation include a multistage tank-type extractor and a single-column vibration column-type apparatus. Providing a water-washing tank on the extract side and washing the extract with water enables formate salt to be removed further efficiently.

<Step (iii): Distillation and Collection Step>

The step (iii) is a step of distilling the extract and collecting hydroxypivalaldehyde from the still residue (distillation and collection step).

The distillation removes the extraction solvent as well as removes impurities having a boiling-point lower than that of HPA. In the extract, HPA, a specific aldehyde solvent as the extraction solvent, and secondary products from IBAL as the raw material are present. In order to facilitate decomposition of the secondary products, additionally, to remove IBAL generated from decomposition of the secondary products and the specific aldehyde solvent by distillation, and, meanwhile, to collect HPA, the distillation is carried out in the presence of water.

The amount of the water which is subjected to the distillation is 100 parts by mass or more and 2,000 parts by mass or less with respect to the total amount, 100 parts by mass, of IBAL and the specific aldehyde solvent in the extract which is subjected to the distillation. Also when a step of concentrating the extract is included after the step (ii) and before the step (iii), the amount of the water which is subjected to the distillation is 100 parts by mass or more and 2,000 parts by mass or less with respect to the total amount, 100 parts by mass, of IBAL and the specific aldehyde solvent in the concentrated extract. The amount of the water which is subjected to the distillation is the total amount of water to be newly added before distillation and water in the extract (oil layer).

When the amount of the water which is subjected to the distillation is less than 100 parts by mass with respect to the total amount, 100 parts by mass, of IBAL and the specific aldehyde solvent, it is difficult to sufficiently decompose and reduce the secondary products, and thus, it is impossible to obtain highly pure HPA. In contrast, when the amount of the water which is subjected to the distillation exceeds 2,000 parts by mass, the amount of the water present is large. Thus, the distillation step requires a longer time, and additionally, a large amount of waste water is generated to thereby cause problems in the viewpoint of environment and productivity.

The amount of the water which is subjected to the distillation is preferably 120 to 1,850 parts by mass, more preferably 150 to 1,700 parts by mass, still more preferably 180 to 1,500 parts by mass with respect to the total amount, 100 parts by mass, of IBAL and the specific aldehyde solvent.

The apparatus used for distillation is not particularly limited, and distillation may be carried out by either a continuous distillation apparatus or a batch-type distillation apparatus. Particularly, the continuous distillation apparatus provides high productivity and also inhibits degradation of HPA, and thus, the yield and quality of HPA tend to be further improved.

In continuous distillation, it is preferred to continuously supply the extract and water while being mixed to the distillation apparatus during distillation. More specifically, it is preferred that the extract and water be mixed in advance and the mixed liquid of the water and extract be continuously supplied to the distillation apparatus.

It is more preferred to continuously supply the extract and water while being mixed and heated to the distillation apparatus. That is, it is preferred that water and the extract be mixed in advance, preheated, and then supplied to the middle stage of the distillation column for flushing. The preheat temperature can be adjusted depending on the extraction solvent used, and is preferably set to a temperature equal to or higher than the boiling point of secondary products from the viewpoint of achieving an effect of reducing the secondary products.

Since the temperature during preheating also depends on the atmosphere pressure in a preheater, the pressure in the preheater is set to preferably 1.0 to 10 atm (0.1013 MPa to 1.013 MPa), more preferably 2 to 8 atm (0.2026 MPa to 0.8106 MPa), still more preferably 2 to 5 atm (0.2026 MPa to 0.5066 MPa). The time required for preheating can be selected as appropriated depending on the type of the extraction solvent and the temperature, and for example, when IBAL is used as the extraction solvent and heating is carried out at 2 to 5 atm, 3 to 60 minutes would be a preferred condition.

In the ease of continuous distillation, when the extract is not concentrated, the amount of the water which is subjected to the distillation is 100 parts by mass or more and 2,000 parts by mass or less, preferably 100 to 1,000 parts by mass, more preferably 150 to 500 parts by mass, still more preferably 150 to 300 parts by mass with respect to the total amount, 100 parts by mass, of isobutyraldehyde derived from the raw material and the aldehyde solvent represented by formula (1) in the extract.

In the case of batch-type distillation, a preferred method is such that water is placed in the distillation still in advance and the extract is supplied dropwise into water in a water reflux state. Heating the extract in contact with water can decompose and reduce secondary products from HPA with IBAL or the specific aldehyde solvent, improving the yield and purity of HPA. The amount of water to be fed in the still in advance, in the case in which the extract is not concentrated, is 100 parts by mass or more and 2,000 parts by mass or less, preferably 100 to 1,000 parts by mass, more preferably 150 to 500 parts by mass, still more preferably 150 to 300 parts by mass with respect to the total amount, 100 parts by mass, of isobutyraldehyde derived from the raw material and the aldehyde solvent represented by formula (1) in the extract.

The batch-type distillation tends to enable thermal degradation of HPA to be inhibited by controlling the pressure and the like as appropriate so as to allow the temperature of the still liquid to be 60 to 100° C. It is only required to adjust the pressure so as to allow the temperature of the still liquid to be more preferably 60 to 90° C., still more preferably 65 to 80° C.

The amount of the water which is subjected to the distillation in the present embodiment, when the extract is not concentrated but distilled, is preferably 50 parts by mass or more and 1,000 parts by mass or less with respect to 100 parts by mass of HPA in the extract. When the amount of the water which is subjected to the distillation is within the range described above, highly pure HPA can be obtained, and the amount of waste water is reduced.

The amount of the water which is subjected to the distillation is more preferably 100 to 800 parts by mass, still more preferably 200 to 600 parts by mass with respect to 100 parts by mass of HPA in the extract.

<Other Steps>

In present embodiment, other steps may be included in addition to the steps (i) to (iii) described above. Specifically, after the step (ii) and before the step (iii), a step of concentrating the extract (hereinbelow, also referred to as a concentration step) may be included. Moreover, after the step (iii), a distilling-out and collection step of further distilling a still residue and collecting HPA as a fraction (hereinbelov, also referred to as a distilling-out and collection step) may be included. Furthermore, after the step (ii) (at any time point after the step (ii)), a step of controlling the content of at least one compound selected from the group consisting of specific compounds described below (hereinbelow, also referred to as a control step) may be included. Hereinbelow, the concentration step, distilling-out and collection step, and control step each will be described.

(Concentration Step)

The method for producing HPA of the present embodiment may include a step of concentrating the extract after the extraction step (step (ii)) and before the distillation and collection step (step (iii)). In the concentration step, IBAL as the raw material and the specific aldehyde solvent as the extraction solvent contained in the extract are distilled off to thereby concentrate HPA. When the concentration step is included, the concentrated extract is distilled in the presence of water in the subsequent step (iii).

When the concentration step is included, the amount of water present can be reduced.

Concentration is carried out such that the total amount of IBAL as the raw material and the specific aldehyde solvent as the extraction solvent reaches preferably 0.1 to 90% by mass, more preferably 1 to 20% by mass, still more preferably 1 to 10% by mass with respect to the amount before concentration. Reducing the amount of IBAL and the specific aldehyde solvent to 90% by mass or less with respect to the amount before concentration can reduce the quantity of heat required for distillation and improve the economic efficiency in the aspect of energy. Carrying out concentration so as to allow the amount of the IBAL and specific aldehyde solvent to be 0.1% by mass or more with respect to the amount before concentration can prevent extension of the time required for concentration.

(Distilling-out and Collection Step)

The method for producing HPA of the present embodiment may include a distilling-out and collection step of further distilling the still residue and collecting HPA as a fraction after the step (iii). When the distilling-out and collection step is included, high-boiling-point impurities such as NPG can be reduced.

In the distilling-out and collection step, the column-top absolute pressure is preferably 1.0 kPa to 1 MPa, more preferably 1.3 kPa to 0.1 MPa, still more preferably 3 kPa to 20 kPa. The column-top temperature is preferably 88 to 150° C., more preferably 90 to 130° C., still more preferably 95 to 115° C.

(Control Step)

The method for producing HPA of the present embodiment may include a step of controlling the content of at least one compound selected from the group consisting of compounds represented by following formulas (2) to (4) after the step (ii). The control step preferably follows the step (iii). The step of controlling the content of the compound described above refers to detecting at least one compound selected from the group consisting of compounds represented by following formulas (2) to (4), contained in the extract obtained after the step (ii) as the extraction step or in hydroxypivalaldehyde obtained after the step (iii) as the distillation and collection step, by, for example, a gas chromatography-hydrogen flame ionization detector (GC-FID) or the like to thereby monitor the content of the compound. The content of at least one compound selected from the group consisting of compounds represented by following formulas (2) to (4) can be specifically measured by the method described in Examples.

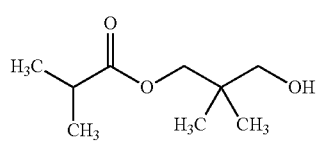

(2)

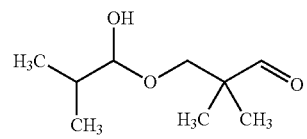

(3)

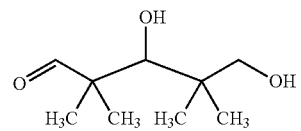

(4)

As mentioned above, the compounds represented by formulas (2) to (4) are secondary products obtained by the reaction of IBAL with HPA. Specifically, the compound represented by formula (2) is an ester of isobutyric acid (hereinbelow, also referred to as IBA) and neopentyl glycol (NPG), i.e. NPG-IBA ester form. The compound represented by formula (3) is an acetal product of HPA and IBAL, and the compound represented by formula (4) is an aldol product of HPA and IBAL. Accordingly, when the specific aldehyde solvent as the extraction solvent is IBAL, including the control step described above is particularly useful. It is assumed that the amount of secondary products can be controlled as well by controlling the content of at least one compound selected from the group consisting of compounds represented by formulas (2) to (4) described above, even when IBAL is also including in the raw material and a specific aldehyde solvent other than IBAL is used as the extraction solvent.

Of these, the compound represented by formula (2) and the compound represented by formula (3), of which removal is difficult by the step (ii), are important, and the compound represented by formula (3) is particularly important. That is, the method for producing HPA of the present embodiment includes preferably a step of controlling the content of the compounds represented by formula (2) and/or formula (3), more preferably a step of controlling the content of the compound represented by formula (3).

In the present embodiment, by distilling the extract in the presence of water, that is, by the step (iii), HPA and IBAL and the specific aldehyde solvent are generated again from the secondary products described above, and IBAL and the specific aldehyde solvent are separated and removed by distillation. Thus, the amount of impurities can be reduced as well as highly pure HPA can be obtained at a high yield.

The compound represented by formula (2) is conceived to be generated by the following reaction mechanism, but such a reaction mechanism is not intended to limit the present invention.

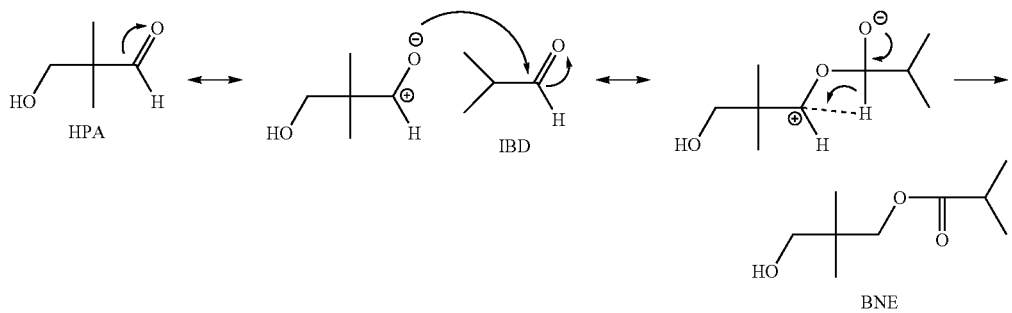

When the content of at least one compound selected from the group consisting of compounds represented by formulas (2) to (4) is controlled, the content is controlled to be preferably 1% by mass or less, more preferably 0.3% by mass or less, still more preferably 0.1% by mass or less, even still more preferably 0.03% by mass or less.

When the content of the compound of formula (3) is controlled, the content is controlled to be preferably 1% by mass or less, more preferably 0.3% by mass or less, still more preferably 0.1% by mass or less, even still more preferably 0.03% by mass or less, yet even still more preferably 0.01% by mass or less.

As mentioned above, controlling the content of the secondary products in HPA obtained can result in more highly pure HPA.

The content of the secondary products, exemplified by compounds represented by formulas (2) to (4), can be controlled by changing mixing conditions such as the amount of water present during distillation, temperature when the extract is mixed with water and mixing time, distillation conditions such as pressure and temperature during distillation, and the like.

[Novel Compound]

The present embodiment relates to a compound represented by following formula (3) and a compound represented by following formula (4).

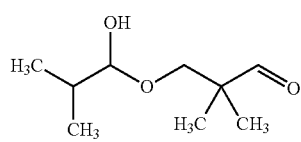 (3)

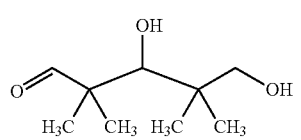 (4)

The compound represented by formula (3) described above and the compound represented by formula (4) described above are novel compounds and are useful as compounds to be controlled as the index for producing highly pure HPA in the method for producing HPA of the present embodiment.

The compound represented by formula (3) and the compound represented by formula (4) can be produced by a production method including a step of reacting IBAL with HPA.

Specifically, the compound represented by formula (3) can be produced by a hemiacetalization reaction of HPA with IBAL. The compound represented by formula (4) can be produced by an aldol reaction of HPA and IBAL. In the aldol reaction, an enol or enolate anion is generated from IBAL, and the enol or enolate anion nucleophilically adds to the aldehyde group of HPA.

In the hemiacetalization reaction described above, it is preferred to react IBAL with HPA in the presence of an acid or basic catalyst.

The acid catalyst is not particularly limited provided that the catalyst is used for an acetalization reaction between aldehyde and alcohol, and examples thereof can include inorganic acids such as hydrochloric acid, sulfuric acid, nitric acid and perchloric acid, and organic acids such as methanesulfonic acid, trifluoromethanesulfonic acid, p-toluenesulfonic acid and benzenesulfonic acid.

The basic catalyst is not particularly limited provided that the catalyst is a catalyst used for an acetalization reaction between aldehyde and alcohol, and examples thereof can include inorganic bases such as potassium carbonate, sodium carbonate, sodium hydrogen carbonate, sodium hydroxide, potassium hydroxide and sodium hydride, and organic bases such as triethylamine, tributylamine, pyridine, N-methylpiperidine and 4-dimethylaminopyridine.

In the aldol reaction described above, it is preferred to react IBAL with HPA in the presence of an acid or basic catalyst.

The acid catalyst is not particularly limited provided that the catalyst is a catalyst that is used for a usual aldol reaction and that generates enol from IBAL, and examples thereof can include inorganic acids such as hydrochloric acid, sulfuric acid, nitric acid and perchloric acid, and organic acids such as methanesulfonic acid, trifluoromethanesulfonic acid, p-toluenesulfonic acid and benzenesulfonic acid.

The basic catalyst is not particularly limited provided that the catalyst is a catalyst that is used for a usual aldol reaction and that generates an enolate anion from IBAL, and examples thereof can include inorganic bases such as potassium, carbonate, sodium carbonate, sodium hydrogen carbonate, sodium hydroxide, potassium hydroxide and sodium hydride, and organic bases such as triethylamine, tributylamine, pyridine, N-methylpiperidine and 4-dimethylaminopyridine.

With respect to the reaction between IBAL and HPA in the presence of an acid or basic catalyst, a hemiacetalization reaction and an aldol reaction may proceed simultaneously. Thus, the reaction product may be a mixture of the compound represented by formula (3) and the compound represented by formula (4). When the product is obtained as a mixture, it is possible to separate the compound represented by formula (3) and the compound represented by formula (4) by recrystallization, silica gel column chromatography, or the like.

The hemiacetalization reaction described above and the aldol reaction described above each can be carried out in a solvent, and the solvent is selected as appropriate in accordance with the reaction temperature, reactants, and the like. The reaction temperature for the organic reaction described above is selected as appropriate in accordance with the conditions such as the boiling point of a solvent used. When a solvent is used in the organic reaction, the reaction solution obtained is concentrated as required, and then, the residue may be used as is in the next reaction. Alternatively, the residue is subjected to appropriate post-treatment, and then may be used as a compound represented by formula (3) or formula (4). Specific examples of the post-treatment method include extraction treatment and/or known purification such as crystallization, recrystallization, and chromatography.

[Hydroxypivalaldehyde]

In HPA to be obtained in the present embodiment, the contents of compounds represented by formula (2), formula (3), and formula (4) are each preferably 0.1% by mass or less. The contents of the compounds represented by formula (2), formula (3), and formula (4) are each more preferably 0.05% by mass or less, still more preferably 0.03% by mass or less.

Of these, in particular, the content of the compound represented by formula (3) is preferably 0.1% by mass or less, more preferably 0.05% by mass or less, still more preferably 0.03% by mass or less, even still more preferably 0.01% by mass or less.

According to the present embodiment, HPA having a low content of the specific impurities (compound represented by formula (2) (neopentyl glycol-isobutyrate ester, compound represented by formula (3) (isobutyraldehyde-hydroxypivalaldehyde-acetal), and compound represented by formula (4) (isobutyraldehyde-hydroxypivalaldehyde-aldol)) described above can be obtained.

The extract in the step (ii) in the present embodiment may contain secondary products, exemplified by compounds represented by formulas (2) to (4), and the content thereof is not particularly limited. The total content of the secondary products, exemplified by the compounds represented by formulas (2) to (4) is preferably 1 to 100 parts by mass, more preferably 1 to 50 parts by mass, still more preferably 1 to 40 parts by mass with respect to 100 parts by mass of HPA in the extract.

EXAMPLES

Hereinbelow, the present invention will be specifically described by Examples, but the present invention is not limited by these Examples in any way. In the following Examples and Comparative Examples, part(s) and % mean part(s) by mass and % by mass, respectively, unless otherwise specified.

In Examples, formaldehyde was quantified by absorbance measurement by means of an acetylacetone method, formate salt was quantified by capillary electrophoresis, and other components were quantified by gas chromatography. The amount of water in the extract oil layer was measured by a Karl Fischer moisture meter (manufactured by HIRANUMA SANGYO Co., Ltd., automatic moisture measuring apparatus AQV-2200, HYDRANAL-Composite 5K manufactured by Hayashi Pure Chemical Ind., Ltd. was used as titration liquid). Conditions for the absorbance measurement, capillary electrophoresis, and gas chromatography are shown below.

[Measurement Methods and Conditions]

<Absorbance Measurement>

Apparatus: Spectrophotometer U3210 manufactured by Hitachi, Ltd.

Measurement wavelength: 420 nm

Color-developing liquid preparation; 75 g of ammonium acetate was dissolved in pure water, and 1.5 mL of glacial acetic acid and 1 mL of acetylacetone were added to the solution. The mixture was diluted with pure water to 1 L.

Sample preparation: 1 mL of 1% sample aqueous solution, 5 mL of pure water, and 10 mL of color-developing liquid were mixed, heated at 40° C. for 30 minutes, and then, cooled to room temperature.

<Capillary Electrophoresis>

Apparatus: G1600A manufactured by Agilent Technologies, Inc.

Electrophoretic fluid: 20 mM quinolinic acid, 39 mM 2-amino-hydroxymethyl-1,3-propanediol, 50 µL/100 mL hexadecyltrimethylammonium hydroxide solution (pH 5.8)

Capillary: fused silica 75 µm, 72 cm (25° C.)

Applied voltage: −20 kV

Detector: diode array (signal: 350 nm (bandwidth 20 nm), reference 230 nm (bandwidth 5 nm))

Sample preparation: formic acid was dissolved in water so as to achieve a concentration of 10 ppm.

<Gas Chromatography (GC)>

Apparatus: Agilent 6890 manufactured by Agilent Technologies, Inc.

Column used: DB-1 (inner diameter 0.53 mm×30 m, film thickness 1.5 µm)

Carrier gas: helium (flow rate in the column 4.5 mL/minute, flow rate control)

Injection: injection port temperature 250° C., split ratio 1:5

Column temperature: retained at 60° C. for 6 minutes, raised at 7° C./minute to 250° C., and retained at 250° C. for 12 minutes Detector: hydrogen flame ionization detector (FID), 250° C.

Sample preparation: HPA was dissolved in acetone so as to achieve a concentration of 1% by mass.

The HPA yield and HPA collecting ratio are calculated as follows.

HPA yield=Total amount of HPA contained in column bottom liquid and distillate liquid after distillation/amount of HPA contained in extract×100 {%}

(in the case of extraction, the total amount of HPA contained in the oil layer and the water layer/the amount of HPA in the raw material×100 [%])

HPA collecting ratio=Amount of HPA contained in column bottom liquid (fraction mainly containing HPA)/HPA amount contained in extract×100 [%]

(in the case of extraction, the total amount of HPA contained in the oil layer/the amount of HPA in the raw material×100 [%])

Reference Example 1

To a 2 L three-necked flask equipped with a stirrer and a cooler, 464 g (6.43 mol) of IBAL and 438 g (5.83 mol) of 40% formalin were fed, and 28 g (0.277 mol) of triethylamine as a catalyst was added thereto while stirring. Stirring was continued at 90° C. for two hours to synthesize HPA. After stirring, the HPA reaction liquid was returned to room temperature, and the components were quantitatively analyzed. The composition of the components of the resulting HPA reaction liquid 930 g is shown in Table 1.

TABLE 1

| Components | Mass (g) | Amount of substance (mol) | Composition (% by mass) |
|---|---|---|---|
| HPA | 596.0 | 5.84 | 64.1 |
| IBAL | 18.6 | 0.26 | 2.0 |
| FA | 8.4 | 0.28 | 0.9 |
| NPG | 10.2 | 0.10 | 1.1 |

TABLE 1-continued

| Components | Mass (g) | Amount of substance (mol) | Composition (% by mass) |
|---|---|---|---|
| Triethylamine | 14.9 | 0.15 | 1.6 |
| Formate salt | 16.7 | 0.11 | 1.8 |
| Water and others | 265.2 | — | 28.5 |
| total | 930.0 | — | 100 |

<Extraction>

To a 2 L three-necked flask equipped with a stirrer and a cooler, 606.7 g of a HPA reaction liquid obtained in the same manner as in Reference Example 1, 601.1 g of IBAL, and 401.93 g of pure water were placed, the temperature of the liquid was adjusted to 60° C., and the mixture was stirred for 60 minutes. After stirring was stopped, the mixture was left to stand for about 10 minutes to be allowed to separate into two layers. The upper layer was collected, 1017.5 g of the extract (oil layer) and 581.8 g of the lower layer (water layer) were obtained.

The HPA reaction liquid was extremely reactive, and thus, the composition of the liquid varies depending on heating time and aging time even after the synthesis reaction. In order to calculate the accurate balance in extraction, the composition of the HPA reaction liquid immediately before this extraction is shown in Table 2, and the composition of the components of the extract is shown in Table 3. The HPA reaction liquid subjected to extraction had a pH of 8.2.

TABLE 2

| Components | Mass (g) | Amount of substance (mol) | Composition (% by mass) |
|---|---|---|---|
| HPA | 373.6 | 3.66 | 61.6 |
| IBAL | 1.1 | 0.02 | 0.2 |
| FA | 3.9 | 0.13 | 0.6 |
| NPG | 14.3 | 0.14 | 2.4 |
| Triethylamine | 9.7 | 0.10 | 1.6 |
| Formate salt | 10.9 | 0.07 | 1.8 |
| Water and others | 193.2 | — | 31.8 |
| total | 606.7 | — | 100 |

TABLE 3

| | Oil layer | | | Water layer | | |
|---|---|---|---|---|---|---|
| Components | Mass (g) | Amount of substance (mol) | Composition (% by mass) | Mass (g) | Amount of substance (mol) | Composition (% by mass) |
| HPA | 300.5 | 2.94 | 29.5 | 20.9 | 0.20 | 3.6 |
| IBAL | 521.4 | 7.23 | 51.2 | 26.6 | 0.37 | 4.6 |
| FA | 0.3 | 0.01 | 0.029 | 0.1 | 0.003 | 0.017 |
| NPG | 11.2 | 0.11 | 1.1 | 2.8 | 0.03 | 0.48 |
| Triethylamine | 0.1 | 0.001 | 0.010 | 97.2 | 0.96 | 16.7 |
| Formate salt | 0.0 | 0.0 | 0.0 | 10.9 | 0.07 | 1.9 |
| Water | 63.2 | 3.51 | 6.2 | 423.3 | 23.5 | 72.8 |
| Others | 120.8 | — | 11.9 | — | — | — |
| total | 1017.5 | — | 100 | 581.8 | — | 100 |

The yield of HPA in the extraction step was 86%. Of 86%, 80.4% was partitioned to the oil layer, and 5.6% was partitioned to the water layer. The remaining 14% is seemed to have formed secondary products with IBAL. The content of FA was 0.1% by mass with respect to HPA, and FA was reduced in extraction in which IBAL was used as the solvent.

Comparative Reference Examples 1 to 8

<Comparison of Extraction Solvents>

Solvent used for extraction included, as ketone solvents, methyl isobutyl ketone (Comparative Reference Example 1) and cyclohexanone (Comparative Reference Example 2), as alcohol solvents, isobutyl alcohol (Comparative Reference Example 3) and octyl alcohol (Comparative Reference Example 4), as ester solvents, ethyl acetate (Comparative Reference Example 5) and butyl acetate (Comparative Reference Example 6), as a hydrocarbon solvent, toluene (Comparative Reference Example 7), and as halogen-containing hydrocarbon solvent, dichloromethane (Comparative Reference Example 8).

To a 200 mL three-necked flask, 45 g of the HPA reaction liquid shown in Table 2, 45 g of the extraction solvent, and 30 g of pure water were added, the temperature of the liquid was adjusted to 60° C., and the mixture was stirred for 60 minutes. After stirring was stopped, the mixture was transferred to a separating funnel and left to stand for about 5 minutes to be allowed to separate into two layers. The upper layer was collected to obtain an extract.

The amounts of the resulting extracts were each as follows: Comparative Reference Example 1: 70.30 g, Comparative Reference Example: 2: 70.25 g, Comparative Reference Example 3: 69.75 g, Comparative Reference Example 4: 70.03 g. Comparative Reference Example 5: 69.85 g, Comparative Reference Example 6: 69.85 g, Comparative Reference Example 7: 67.99 g, and Comparative Reference Example 8: 76.15 g.

The composition of the components of each resulting extract is shown in Table 4.

TABLE 4

| Components | Mass (g) | Amount of substance (mmol) | Composition (% by mass) | Mass (g) | Amount of substance (mmol) | Composition (% by mass) | Mass (g) | Amount of substance (mmol) | Composition (% by mass) | Mass (g) | Amount of substance (mmol) | Composition (% by mass) |
|---|---|---|---|---|---|---|---|---|---|---|---|---|
| | Comparative Reference Example 1 (Methyl isobutyl ketone) | | | Comparative Reference Example 2 (Cyclohexane) | | | Comparative Reference Example 3 (Isobutyl alcohol) | | | Comparative Reference Example 4 (Octyl alcohol) | | |
| HPA | 23.2 | 227.2 | 33.0 | 22.9 | 224.2 | 32.6 | 22.6 | 221.3 | 32.4 | 22.9 | 224.2 | 32.7 |
| IBAL | 0.1 | 1.1 | 0.1 | 0.9 | 12.2 | 1.3 | 0.8 | 11.5 | 1.2 | 0.9 | 12.8 | 1.3 |
| FA | 0.3 | 9.7 | 0.4 | 0.3 | 9.7 | 0.4 | 0.3 | 9.7 | 0.4 | 0.3 | 9.7 | 0.4 |
| NPG | 1.1 | 10.2 | 1.5 | 0.5 | 4.3 | 0.6 | 0.5 | 4.8 | 0.7 | 0.5 | 4.9 | 0.7 |
| Triethylamine | 0.7 | 7.2 | 1.0 | 0.7 | 6.5 | 0.9 | 0.6 | 6.3 | 0.9 | 0.5 | 4.9 | 0.7 |
| Formate salt | 0.0 | 0.0 | 0.0 | 0.0 | 0.0 | 0.0 | 0.0 | 0.0 | 0.0 | 0.0 | 0.0 | 0.0 |
| HPA Collecting ratio (%) | | 83.9 | | | 82.8 | | | 81.8 | | | 82.8 | |
| FA/HPA (% by mass) | | 1.2 | | | 1.3 | | | 1.3 | | | 1.3 | |
| | Comparative Reference Example 5 (Ethyl acetate) | | | Comparative Reference Example 6 (Butyl acetate) | | | Comparative Reference Example 7 (Toluene) | | | Comparative Reference Example 8 (Dichloromethane) | | |
| HPA | 22.7 | 222.3 | 32.5 | 22.7 | 222.3 | 32.5 | 20.6 | 201.7 | 30.3 | 22.8 | 223.2 | 32.5 |
| IBAL | 0.9 | 12.5 | 1.3 | 0.9 | 12.1 | 1.2 | 0.8 | 11.2 | 1.2 | 0.8 | 11.2 | 1.2 |
| FA | 0.2 | 6.0 | 0.3 | 0.2 | 5.7 | 0.2 | 0.3 | 9.3 | 0.4 | 0.2 | 5.7 | 0.2 |
| NPG | 0.5 | 4.8 | 0.7 | 0.5 | 4.6 | 0.7 | 0.5 | 4.7 | 0.7 | 0.6 | 5.7 | 0.8 |
| Triethylamine | 0.7 | 7.2 | 1.0 | 0.7 | 6.7 | 1.0 | 0.8 | 7.6 | 1.1 | 0.9 | 8.7 | 1.3 |
| Formate salt | 0.0 | 0.0 | 0.0 | 0.0 | 0.0 | 0.0 | 0.0 | 0.0 | 0.0 | 0.0 | 0.0 | 0.0 |
| HPA Collecting ratio (%) | | 82.1 | | | 82.1 | | | 74.4 | | | 82.5 | |
| FA/HPA (% by mass) | | 0.8 | | | 0.8 | | | 1.4 | | | 0.7 | |

In Table 4, FA/HPA represents the mass percentage of FA with respect to HPA.

With any of the solvents used, 0.7 to 1.4% by mass of FA remained with respect to HPA, and 0.1% by mass in Reference Example 1, of which solvent is IBAL, was not achieved. It was confirmed that none of the solvent formed secondary products with HPA.

[Comparison of Properties of Liquids During Extraction]

Comparative Reference Example 9

Distillation of 105 g of the HPA reaction liquid shown in Table 1 at a column-top absolute pressure of 0.082 MPa and a column-top temperature of 58.0° C. provided 97.46 g of a still residue. As shown in Table 5, it was confirmed that triethylamine was removed from the composition of components contained in the still residue.

TABLE 5

| Components | Mass (g) | Amount of substance (mmol) | Composition (% by mass) |
|---|---|---|---|
| HPA | 67.1 | 657 | 68.8 |
| IBAL | 1.0 | 14 | 1.0 |
| FA | 0.9 | 30 | 0.9 |
| NPG | 1.1 | 11 | 1.1 |

TABLE 5-continued

| Components | Mass (g) | Amount of substance (mmol) | Composition (% by mass) |
|---|---|---|---|
| Triethylamine | 0.1 | 0.63 | 0.1 |
| Formate salt | 1.8 | 12 | 1.8 |
| Water and others | 25.6 | — | 26.3 |
| Total | 97.5 | — | 100 |

Taken was 45 g of the still residue, which was subjected to extraction in the same manner as in Reference example 1. Specifically, to 45 g of still residue, 30 g of pure water and 45 g of an isobutyraldehyde solvent were added, and the mixture was subjected to extraction.

The composition of the resulting extract (74.4 g) is shown, in Table 6.

TABLE 6

| Components | Mass (g) | Amount of substance (mmol) | Composition (% by mass) |
|---|---|---|---|
| HPA | 28.6 | 280 | 38.4 |
| IBAL | 41.6 | 577 | 55.9 |
| FA | 0.3 | 10 | 0.4 |
| NPG | 0.3 | 3 | 0.4 |
| Triethylamine | 0.0 | 0.0 | 0.0 |
| Formate salt | 0.0 | 0.0 | 0.0 |
| Water and others | 3.6 | — | 4.9 |
| total | 74.4 | — | 100 |

The collecting ratio of HPA from the still residue was 96.47%, and 1.1% by mass of formaldehyde remained with respect to HPA. Formation of secondary products from HPA and IBAL was not confirmed. Due to absence of base such as triethylamine, the pH during extraction was less than 7.5. When distillation precedes extraction, triethylamine is removed, and the collecting ratio of HPA is high. However, FA was not sufficiently reduced during the extraction operation, it was shown that this disrupted extraction.

Example 1

[Continuous Distillation]

An extract obtained by the operation same as in Reference Example 1, while being mixed at a flow rate of 2.5 g/minute with water having a flow rate of 3.0 g/minute, was passed through, at an absolute pressure of 0.33 MPa and with a dwell time in preheater of 10 minutes, a stainless double-pipe heat exchanger having an outer pipe, through which steam having an absolute pressure of 0.6 MPa was passed, to thereby be supplied to a point at the column height of 500 mm of a distillation column having a column diameter of 38 mm and a column height of 800 mm, packed with φ3 mm Dickson packing. Here, the content of IBAL in the extract was 51.2% by mass, and the flow rate of IBAL was 1.28 g/minute (0.512×2.5 g/minute=1.28 g/minute). The content of water in the extract was 6.2% by mass, and the flow rate of water supplied from the extract was 0.155 g/minute (0.062×2.5 g/minute=0.16 g/minute). Thus, the amount of the water which is subjected to the distillation was 247 parts by mass ((3.0+0.16)/1.28×100=247) with respect to the total amount, 100 parts by mass, of the total amount of IBAL derived from the raw material and IBAL used as the specific aldehyde solvent in the extract. Distillation was carried out at the column-top absolute pressure of 0.032 MPa of the distillation column. After the column top temperature reached 70.1° C., the column bottom liquid and distillate liquid were sampled for 60 minutes, and 71.7 g of the column bottom liquid and 257.3 g of the distillate liquid were obtained. The composition of each of the resulting liquids is shown in Table 7.

TABLE 7

| | Column bottom liquid | | | Distillate liquid | | |
|---|---|---|---|---|---|---|
| Components | Mass (g) | Amount of substance (mmol) | Composition (% by mass) | Mass (g) | Amount of substance (mmol) | Composition (% by mass) |
| HPA | 49.2 | 482 | 68.6 | 1.8 | 17.6 | 0.7 |
| IBAL | 0.031 | 0.43 | 0.0 | 76.8 | 1065 | 29.8 |
| FA | 0.007 | 0.23 | 0.0 | 0.0 | 0.0 | 0.0 |
| NPG | 1.5 | 14 | 2.1 | 0.0 | 0.0 | 0.0 |
| Triethylamine | 0.0 | 0.0 | 0.0 | 0.015 | 0.15 | 0.0 |
| Formate salt | 0.0 | 0.0 | 0.0 | 0.0 | 0.0 | 0.0 |
| Water and others | 21.0 | — | 29.3 | 178.7 | — | 69.4 |
| total | 71.7 | — | 100 | 257.3 | — | 100 |

From the composition of the column bottom liquid, the content of IBAL decreased to 0.043% by mass (0.0% by mass in the table) by distillation. The yield of HPA in the distillation operation was 115%, of which 111.2% was contained in the column bottom liquid. This showed that the secondary products of HPA and IBAL generated during extraction returned to HPA again, which was then collected. The total collecting ratio of HPA from the extraction of Reference Example 1 and the distillation of Example 1 was 89.40%.

Example 2

[Batch-type Distillation]

The extract of Reference Example 1 was supplied to a distillation apparatus under water reflux and distilled.

Into a distillation still having a capacity of 2 L equipped with a distillation column having a column diameter of 10 mm and a column height of 180 mm packed with Sulzer packing, 502.6 g of water was fed and heated to reflux at a column-top pressure of 0.033 MPa. While water was refluxed, 494.80 g of the extract obtained in Reference Example 1 was added dropwise at a flow rate of 25.5 to 42 g/minute into the distillation still. Here, the content of IBAL in the extract was 51.2% by mass, and 253.34 g of IBAL was contained in 434.80 g of the extract. Here, the content of water in the extract was 6.2% by mass, and 30.68 g of water was contained in 494.80 g of the extract. Thus, the amount of the water which is subjected to the distillation was 210 parts by mass ((502.6+30.68)/253.34×100=210) with respect to the total amount, 100 parts by mass, of the total amount of IBAL derived from the raw material and IBAL used as the specific aldehyde solvent in the extract. While the temperature of the liquid in the still was maintained at 67 to 73° C., the column-top absolute pressure was reduced to 0.024 MPa. When the content of IBAL in the liquid inside the still decreased to less than 0.1%, distillation was finished. As the column bottom liquid, 413.8 g of a distillate liquid was obtained together with the liquid inside the still of 580.9 g, which liquids were separated into two layers. The composition of each of the resulting liquids is shown in Table 8.

TABLE 8

| | Column bottom liquid | | | Distillate liquid | | |
|---|---|---|---|---|---|---|
| Components | Mass (g) | Amount of substance (mmol) | Composition (% by mass) | Mass (g) | Amount of substance (mmol) | Composition (% by mass) |
| HPA | 167.3 | 1638 | 28.8 | 0.90 | 8.8 | 0.2 |
| IBAL | 0.50 | 6.9 | 0.1 | 256.3 | 3554 | 61.9 |
| FA | 0.30 | 10 | 0.1 | 0.0 | 0.0 | 0.0 |
| NPG | 5.3 | 51 | 0.9 | 0.0 | 0.0 | 0.0 |
| Triethylamine | 0.10 | 1.0 | 0.0 | 0.0 | 0.0 | 0.0 |
| Formate salt | 0.0 | 0.0 | 0.0 | 0.0 | 0.0 | 0.0 |
| Water and others | 407.4 | — | 70.1 | 156.6 | — | 37.8 |
| total | 580.9 | — | 100 | 413.8 | — | 100 |

From the composition of the column bottom liquid, the content of IBAL decreased to 0.086% by mass (0.1% by mass in the table) by distillation. The yield of HPA in the distillation operation was 115.2%. It was showed that the secondary product of HPA and IBAL generated during extraction was able to return to HPA again and then be collected.

The total collecting ratio of HPA was 92.46%.

Comparative Example 1

[Continuous Distillation Without Coexisting Water]

Only 230.1 g of an extract obtained in the same manner as in Reference Example 1 was supplied at a flow rate of 3.8 g/minute to a distillation apparatus through a stainless double-pipe heat exchanger in the same manner as in Example 1 to thereby be distilled. Obtained were 87.9 g of a column bottom liquid and 129.5 g of a distillate liquid. The composition of each of the resulting liquids is shown in Table 9.

TABLE 9

| | Column bottom liquid | | | Distillate liquid | | |
|---|---|---|---|---|---|---|
| Components | Mass (g) | Amount of substance (mmol) | Composition (% by mass) | Mass (g) | Amount of substance (mmol) | Composition (% by mass) |
| HPA | 74.3 | 728 | 84.5 | 3.90 | 38.2 | 3.0 |
| IBAL | 1.60 | 22.2 | 1.8 | 116.3 | 1613 | 89.8 |
| FA | 0.0 | 0.0 | 0.0 | 0.0 | 0.0 | 0.0 |
| NPG | 2.53 | 24 | 2.9 | 0.0 | 0.0 | 0.0 |
| Triethylamine | 0.0 | 0.0 | 0.0 | 0.023 | 0.23 | 0.0 |
| Formate salt | 0.0 | 0.0 | 0.0 | 0.0 | 0.0 | 0.0 |
| Water and others | 9.50 | — | 10.8 | 9.3 | — | 7.2 |
| total | 87.9 | — | 100 | 129.5 | — | 100 |

The total collecting ratio of HPA from both the extraction of Reference Example 1 and the distillation of Comparative Example 1 was 88.0%. In the distillation of this Comparative Example, in which mixing and heating with water were not carried out, 1.8% by mass of IBAL remained. When water was not allowed to be present, the secondary products of HPA and IBAL were insufficiently decomposed. Thus, it was shown that the yield of HPA was also low and the concentration of IBAL was also high.

Comparative Example 2

[Continuous Distillation in the Presence of a Small amount of Water]

While being mixed at a flow rate of 3.9 g/minute with water having a flow rate of 0.41 g/minute, 233.1 g of an extract obtained in the same manner as in Reference Example 1 was supplied to a distillation apparatus through a stainless double-pipe heat exchanger in the same manner as in Example 1 to thereby be distilled. Here, the content of IBAL in the extract was 51.2% by mass, and the flow rate of IBAL was 2.00 g/minute (0.512×3.9 g/minute=2.00 g/minute). The content of water in the extract was 6.2% by mass, and the flow rate of water supplied from the extract was 0.24 g/minute (0.062×3.9 g/minute=0.24 g/minute). Thus, the amount of the water which is subjected to the distillation was 32.5 parts by mass ((0.41+0.24)/2.00× 100=32.5) with respect to the total amount, 100 parts by mass, of IBAL derived from the raw material and IBAL used as the specific aldehyde solvent, in the extract.

Distillation was carried out in the same manner as in Example 1, and 86.6 g of a column bottom liquid and 170.2 g of a distillate liquid were obtained. The composition of each of the resulting liquids is shown in Table 10.

TABLE 10

| Components | Column bottom liquid | | | Distillate liquid | | |
|---|---|---|---|---|---|---|
| | Mass (g) | Amount of substance (mmol) | Composition (% by mass) | Mass (g) | Amount of substance (mmol) | Composition (% by mass) |
| HPA | 73.1 | 716 | 84.4 | 6.10 | 59.7 | 3.6 |
| IBAL | 0.55 | 7.6 | 0.6 | 118.9 | 1649 | 69.8 |
| FA | 0.026 | 0.87 | 0.0 | 0.0 | 0.0 | 0.0 |
| NPG | 2.56 | 24.6 | 3.0 | 0.0 | 0.0 | 0.0 |
| Triethylamine | 0.0 | 0.0 | 0.0 | 0.0 | 0.0 | 0.0 |
| Formate salt | 0.0 | 0.0 | 0.0 | 0.023 | 0.16 | 0.0 |
| Water and others | 10.4 | — | 12.0 | 45.2 | — | 26.6 |
| total | 86.6 | — | 100 | 170.2 | — | 100 |

The total collecting ratio of HPA from the reaction liquid of Reference Example 1 was 85.4%. Also when the amount of water supplied was insufficient as in the distillation of this Comparative Example, 0.63% by mass (0.6% by mass in the table) of IBAL remained.

Comparative Example 3

[Distillation of Extract Without Supplying Water (Consequently, Concentration)]

Without water supplied, 382.7 g of an extract obtained in the same manner as in Reference Example 1 was distilled in the same manner as in Example 1. IBAL was distilled off as a distillate liquid, and 145.3 g of a concentrate in which the content of IBAL in a column bottom liquid was reduced to 1.9% by mass was obtained as the column bottom liquid. Also, 237.3 g of a distillate liquid was obtained. Water in the column bottom liquid was quantified by a Karl Fischer moisture meter. The composition of each of the resulting liquids is shown in Table 11.

TABLE 11

| Components | Column bottom liquid | | | Distillate liquid | | |
|---|---|---|---|---|---|---|
| | Mass (g) | Amount of substance (mmol) | Composition (% by mass) | Mass (g) | Amount of substance (mmol) | Composition (% by mass) |
| HPA | 128.3 | 1256 | 88.2 | 11.2 | 110 | 4.72 |
| IBAL | 2.70 | 37.4 | 1.9 | 226.0 | 3134 | 95.2 |
| FA | 0.33 | 11 | 0.23 | 0.0 | 0.0 | 0.0 |
| NPG | 2.10 | 20 | 1.5 | 0.07 | 0.69 | 0.030 |
| Triethylamine | 0.13 | 1.3 | 0.090 | 0.0 | 0.0 | 0.0 |
| Formate salt | 0.0 | 0.0 | 0.0 | 0.0 | 0.0 | 0.0 |
| Water | 2.4 | 0.1 | 1.6 | 0.13 | 7 | 0.05 |
| Others | 9.4 | — | 6.5 | — | — | — |
| total | 145.3 | — | 100 | 237.4 | — | 100 |

Example 3

[Distillation of Concentrate]

In the same manner as in Example 1, 141.6 g of the column bottom liquid (concentrate) obtained in Comparative Example 3 was supplied at a flow rate of 3.5 g/minute, together with water at a flow rate of 0.87 g/minute, to a distillation apparatus through a stainless double-pipe heat exchanger to thereby be distilled. Here, the content of IBAL in the column bottom liquid was 1.9% by mass, and the flow rate of IBAL was 0.066.5 g/minute (0.019×3.5 g/minute=0.0665 g/minute). The content of water in the column bottom liquid was 1.6% by mass, and the flow rate of water supplied from the column bottom liquid was 0.056 g/minute. Thus, the amount of the water which is subjected to the distillation was 1.392 parts by mass ((0.87+0.056)/0.0665× 100=1.392) with respect to the total amount, 100 parts by mass, of IBAL derived from the raw material and IBAL used as the specific aldehyde solvent in the extract.

By a distillation operation, 135.0 g of a column bottom liquid and 41.7 g of a distillate liquid were obtained. The composition of each of the resulting liquids is shown in Table 12.

TABLE 12

| Components | Column bottom liquid | | | Distillate liquid | | |
|---|---|---|---|---|---|---|
| | Mass (g) | Amount of substance (mmol) | Composition (% by mass) | Mass (g) | Amount of substance (mmol) | Composition (% by mass) |
| HPA | 118.2 | 1157 | 87.6 | 6.70 | 65.6 | 16.1 |
| IBAL | 0.09 | 1.2 | 0.1 | 3.5 | 49 | 8.4 |
| FA | 0.32 | 11 | 0.2 | 0.0 | 0.0 | 0.0 |
| NPG | 2.4 | 23 | 1.8 | 0.0 | 0.0 | 0.0 |
| Triethylamine | 0.13 | 1.3 | 0.1 | 0.0 | 0.0 | 0.0 |
| Formate salt | 0.0 | 0.0 | 0.0 | 0.0 | 0.0 | 0.0 |
| Water and others | 13.8 | — | 10.3 | 31.5 | — | 75.5 |
| Total | 135.0 | — | 100 | 41.7 | — | 100 |

From the composition of the column bottom liquid, the content of IBAL decreased to 0.060% by mass (0.1% by mass in Table 12) by distillation. The yield of HPA in this distillation operation was 94.6%. Reduction in the concentration of IBAL by the concentration operation before distillation was able to reduce water supplied during distillation.

Example 4

[Distillation Purification of HPA]

While warmed to 105° C., 95.3 g of the column bottom liquid obtained in the same manner as in Example 1 was supplied to a point at the column height of 500 mm of a distillation column having a column diameter of 30 mm and a column height of 800 mm, packed with φ3 mm Dickson packing. Distillation was carried out at the column-top absolute pressure of 0.008 MPa of the distillation column. After the column top temperature reached 104° C., a distillate liquid was sampled, and 56.7 g of distillate liquid as a distillation purified product of HPA and 36.7 g of a column bottom liquid were obtained. The composition of each of the resulting liquids is shown in Table 13.

TABLE 13

| Components | Column bottom liquid | | | Distillate liquid | | |
|---|---|---|---|---|---|---|
| | Mass (g) | Amount of substance (mmol) | Composition (% by mass) | Mass (g) | Amount of substance (mmol) | Composition (% by mass) |
| HPA | 9.39 | 92 | 25.6 | 55.80 | 546 | 98.4 |
| IBAL | 0.01 | 0.1 | 0.0 | 0.09 | 1 | 0.2 |
| Formaldehyde | 0.02 | 1 | 0.1 | 0.0 | 0.0 | 0.0 |
| NPG | 2.26 | 22 | 6.2 | 0.0 | 0.0 | 0.0 |
| Triethylamine | 0.0 | 0.0 | 0.0 | 0.0 | 0.0 | 0.0 |
| Formate salt | 0.0 | 0.0 | 0.0 | 0.0 | 0.0 | 0.0 |
| Water and others | 25.0 | — | 68.2 | 0.82 | — | 1.4 |
| total | 36.7 | — | 100 | 56.7 | — | 100 |

The content of NPG in HPA obtained as the distillate liquid decreased to 0.033% by mass (0.0% by mass in Table 13), and it was confirmed that further distillation was able to reduce high-boiling-point impurities such as NPG.

Example 5

[Control of Impurities]
<Reaction Step and Extraction Step>

In the same manner as in Reference Example 1, 4.640 g (64.3 mol) of IBAL and 4.380 g (58.3 mol) of 40% formalin were fed, and 280 g (2.77 mol) of triethylamine as a catalyst was added to the mixture with stirring. Stirring at 90° C. was continued for 2 hours to thereby synthesize HPA.

To a three-necked flask equipped with a stirrer and a cooler, 5,953.4 g of a HPA reaction liquid obtained in the same manner as in Reference Example 1, 5,947 g of IBAL, 3,445 g of pure water were placed, the temperature of the liquid was adjusted to 60° C., and the mixture was stirred for 60 minutes. After stirring was stopped, the mixture was left to stand for about 10 minutes to be allowed to separate into two layers. The upper layer was collected, 9,855.4 g of the extract (oil layer) and 5,484.8 g of the lower layer (water layer) were obtained.

The HPA reaction liquid is extremely reactive, and thus, the composition of the liquid varies depending on heating time and aging time even after the synthesis reaction. In order to calculate the accurate balance in extraction, the composition of the HPA reaction liquid immediately before this extraction and the composition of the components of the extract are shown in Table 14.

TABLE 14

| Components | Reaction liquid (after heating and aging) | | Oil layer | | Water layer | |
|---|---|---|---|---|---|---|
| | Mass (g) | Composition (% by mass) | Mass (g) | Composition (% by mass) | Mass (g) | Composition (% by mass) |
| IBAL | 11.10 | 0.19 | 5213.40 | 54.15 | 265.97 | 4.85 |
| FA | 55.43 | 0.93 | 0.00 | 0.00 | 49.49 | 0.90 |
| Isobutyric acid | 0.00 | 0.00 | 89.72 | 0.93 | 0.00 | 0.00 |
| DMEA | 29.71 | 0.50 | 0.65 | 0.01 | 29.10 | 0.53 |
| DEMA | 31.69 | 0.53 | 1.08 | 0.01 | 30.31 | 0.55 |
| TEA | 51.49 | 0.86 | 1.23 | 0.01 | 47.98 | 0.87 |
| HPA | 3735.70 | 62.75 | 2777.88 | 28.85 | 208.46 | 3.80 |
| NPG | 143.46 | 2.41 | 111.78 | 1.16 | 28.54 | 0.52 |
| FNE | 0.96 | 0.02 | 0.00 | 0.00 | 0.00 | 0.00 |
| HPAc | 0.00 | 0.00 | 0.00 | 0.00 | 0.00 | 0.00 |
| HPA-NPG | 0.00 | 0.00 | 0.00 | 0.00 | 0.00 | 0.00 |
| ESG | 42.34 | 0.71 | 81.67 | 0.85 | 2.14 | 0.04 |
| Water | 1836.30 | 30.84 | 585.81 | 6.08 | 4690.10 | 85.51 |
| BNE | 6.37 | 0.11 | 329.50 | 3.42 | 58.56 | 1.07 |
| IBAL-HPA acetal | 0.00 | 0.00 | 405.04 | 4.21 | 0.00 | 0.00 |
| IBAL-HPA aldol | 8.89 | 0.15 | 30.14 | 0.31 | 74.11 | 1.35 |
| total | 5953.4 | 100 | 9627.9 | 100 | 5484.8 | 100 |

Abbreviations in Table 14 are as follows. The identifying and detecting method for each component is shown in the parentheses.

IBAL: isobutyraldehyde (GC-FID (gas chromatography-hydrogen flame ionization detector))
FA: formaldehyde (absorptiometer (acetylacetone method))
DMEA: dimethylethylamine (capillary electrophoresis)
DEMA: diethylmethylamine (capillary electrophoresis)
TEA: triethylamine (capillary electrophoresis)
HPA: hydroxypivalaldehyde (GC-FID)
NPG: neopentyl glycol (GC-FID)
FNE: neopentyl glycol-formate ester (GC-FID)
HPAc: hydroxypivalic acid (capillary electrqphoresis)
HPA-NPG: hydroxypivalaldehyde-neopentyl glycol-acetal (GC-FID)
ESG: neopentyl glycol-hydroxypivalate (GC-FID)
BNE: neopentyl glycol-isobutyrate ester (compound represented by formula (2)) (GC-FID)
IBAL-HPA acetal: isobutyraldehyde-hydroxypivalaldehyde-acetal (compound represented by formula (3)) (GC-FID)
IBAL-HPA aldol: isobutyraldehyde-hydroxypivalaldehyde-aldol (compound represented by formula (4) (GC-FID)

<Identification of Control Impurities>

BNE was synthesized as a preparation by condensation of isobutyryl chloride and BPG in accordance with the method described in WO2009/33079. The resulting preparation BNE was detected by gas chromatography at the same retention time as an impurity component BNE in Table 14. In gas chromatography equipped with a mass spectrometer, the mass spectrum of the preparation corresponded to that of the impurity product BNE. The spectrum data of the BNE preparation were as follows.

$^1$H NMR (500 MHz, CDCl$_3$): chemical shift 0.93 (s, 6H), 1.19 (d, J=7.0 Hz, 6H), 2.30 (t, J=6.3 Hz, 2H), 2.59 (sept, J=7.0 Hz, 1H), 3.28 (d, J=6.3 Hz, 2H), 3.94 (s, 2H) ppm
HRMS (EI$^+$); m/z [M−31]$^+$ calcd for C$_8$H$_{15}$O$_2$ (M-CH$_2$OH): 143.10720; found; 143.10719.

From a sample containing the compounds of formula (3) and formula (4), two peaks of M−1 (m/z173), which is seen in the EI+ spectrum of an aliphatic aldehyde, were observed, and m/z 73 and 103, which corresponded to peaks generated by cleavage to monomers as the CI+ spectrum, were observed.

The compound of formula (3) and the compound of formula (4) had different retention times until when the M−1 (m/z 173) spectrum was observed. The compound of formula (4) has a molecular structure having more hydroxyl groups as polar functional groups, and thus, the peak of which retention time was short was taken as the compound of formula (4). The peak of which retention time was short was taken as the compound of formula (3).

The spectrum data of the compound of formula (3) were as follows.
HRMS (EI$^+$): m/z [M−1]$^+$ calcd for C$_9$H$_{17}$O$_3$: 173.11777; found; 173.11926.

The spectrum data of the compound of formula (4) were as follows.
HRMS (EI$^+$): m/z [M−1]$^+$ calcd for C$_9$H$_{17}$O$_3$: 173.11777; found; 173.11863.

<Distillation and Collection Step>

To a reaction still equipped with a distillation column and a stirrer, 10052 g of water was fed. After the pressure was reduced to 248 torr, water was heated to be fully refluxed. Into the water in the reaction still, 9586.85 g of the extract obtained in Example 5 was supplied at a flow rate of 25.5 to 42.0 g/minute. Here, the content of IBAL in the extract was 54.15% by mass, and the amount of IBAL in the extract was 5191.3 g (0.5415×9586.85 g=5191.3 g). The content of water in the extract was 6.08% by mass, and the amount of water supplied from the extract was 582.9 g (0.0608× 9586.85 g =582.9 g). Thus, the amount of water which is subjected to the distillation was: 205 parts by mass ((10052+ 582.9)/5186.5×100=205) with respect to the total amount, 100 parts by mass, of IBAL derived from the raw material and IBAL used as the specific aldehyde solvent in the extract. As the extract was supplied, the temperature of the still liquid gradually increases. Thus, IBAL and water were boiled while the pressure reduction degree was adjusted such that the temperature of the still reached 67.6 to 72.6° C. After the distillate liquid became only one layer (water layer) and water was boiled for a while, the still liquid was sampled. Sufficient reduction in the HPA-IBAL reactant and IBAL was confirmed, and distillation was finished. Stirring of the still liquid was stopped. After the still liquid was separated into two layers, the oil layer and the water layer were each collected.

The analysis results of the extract subjected to the distillation and collection step (raw material), the oil layer of the resulting distillate portion (distillate oil layer), the water layer of the resulting distillate portion (distillate water layer), and still residue were shown below.

From the analysis results of the still residue, the yield of HPA of the distillation operation was 120.9%. This showed that the secondary products of HPA and IBAL generated during extraction returned to HPA again, which then was able to be collected. The total collecting ratio of HPA from a reaction liquid obtained by combining extraction of Example 5 and distillation of Example 6 was 89.9%.

wherein R represents a saturated alkyl group having 3 or more and 7 or less carbon atoms, wherein said distilling occurs in the presence of water, and an amount of water which is subjected to said distilling is 100 parts by mass or more and 2,000 parts by mass or less with respect to a total amount, 100 parts by mass, of isobutyraldehyde derived from a raw material and an aldehyde solvent represented by the formula (1) in the extract which is subjected to said distilling.

TABLE 15

|  | Raw material | | Distillate oil layer | | Distillate water layer | | Still residue | |
| --- | --- | --- | --- | --- | --- | --- | --- | --- |
|  | Mass (g) | Composition (% by mass) | Mass (g) | Composition (% by mass) | Mass (g) | Composition (% by mass) | Mass (g) | Composition (% by mass) |
| Isobutyl alcohol | 0.00 | 0.00 | 1.70 | 0.03 | 0.83 | 0.03 | 0.00 | 0.00 |
| IBAL | 5191.17 | 54.15 | 4989.80 | 95.00 | 136.06 | 5.67 | 9.96 | 0.06 |
| FA | 0.00 | 0.00 | 1.00 | 0.02 | 0.00 | 0.00 | 0.00 | 0.00 |
| Isobutyric acid | 89.34 | 0.93 | 147.13 | 2.80 | 7.77 | 0.32 | 0.00 | 0.00 |
| DEMA | 0.65 | 0.01 | 0.00 | 0.00 | 0.00 | 0.00 | 0.54 | 0.00 |
| DEMA | 1.08 | 0.01 | 0.00 | 0.00 | 0.00 | 0.00 | 0.71 | 0.01 |
| TEA | 1.22 | 0.01 | 0.00 | 0.00 | 0.14 | 0.01 | 0.79 | 0.01 |
| HPA | 2766.04 | 28.85 | 8.00 | 0.15 | 9.01 | 0.38 | 3345.10 | 28.53 |
| NPG | 111.30 | 1.16 | 0.00 | 0.00 | 0.00 | 0.00 | 105.18 | 0.90 |
| FNE | 0.00 | 0.00 | 0.00 | 0.00 | 0.00 | 0.00 | 0.00 | 0.00 |
| ESG | 81.32 | 0.85 | 0.00 | 0.00 | 0.00 | 0.00 | 33.31 | 0.28 |
| Water | 583.31 | 6.08 | 101.38 | 1.93 | 2245.00 | 93.54 | 8221.10 | 70.13 |
| BNE | 328.10 | 3.42 | 1.88 | 0.04 | 0.61 | 0.03 | 4.02 | 0.03 |
| IBAL-HPA acetal | 403.31 | 4.21 | 1.43 | 0.03 | 0.55 | 0.02 | 0.00 | 0.00 |
| IBAL-HPA aldol | 30.01 | 0.31 | 0.00 | 0.00 | 0.00 | 0.00 | 2.12 | 0.02 |
| total | 9586.85 | 100 | 5252.32 | 100 | 2399.97 | 100 | 11722.83 | 100 |

In extraction, the compound represented by formula (2) and the compound represented by formula (3) remained, and the content of the compound represented by formulas (2) to (4) in the still residue was confirmed to be 0.1% by mass or less by distillation in the presence of water.

Particularly, it is difficult to remove the compound represented by formula (3) by extraction, but the compound was significantly reduced by distillation in the presence of water. The content was confirmed to be 0.01% by mass or less.

According to the production method of the present embodiment, it is possible to produce HPA in which specific impurities are reduced by removing formate salt and FA from HPA synthesized from FA and IBAL by extraction and removing other impurities by distillation.

The present application is based on Japanese Patent Application No. 2016-001698 filed Jan. 7, 2016, the content of which is incorporated herein by reference.

The invention claimed is:

1. A method for producing hydroxypivalaldehyde, the method comprising reacting isobutyraldehyde with formaldehyde to obtain a reaction solution containing hydroxypivalaldehyde, subsequently extracting the reaction solution with an aldehyde solvent represented by formula (1) under basicity to obtain an extract containing hydroxypivalaldehyde, and subsequently distilling the extract and then collecting hydroxypivalaldehyde from a still residue:

2. The method according to claim 1, wherein the amount of water which is subjected to said distilling is 50 parts by mass or more and 1,000 parts by mass or less with respect to 100 parts by mass of hydroxypivalaldehyde in the extract which is subjected to said distilling.

3. The method according to claim 1, further comprising concentrating the extract after said extracting and before said distilling.

4. The method according to claim 1, wherein the aldehyde solvent represented by the formula (1) is isobutyraldehyde.

5. The method according to claim 1, wherein said distilling and said collecting are carried out by continuously supplying the extract and water, while being mixed, to a distillation apparatus and collecting hydroxypivalaldehyde from the still residue.

6. The method according to claim 1, wherein said distilling and said collecting are carried out by continuously supplying the extract and water, while being mixed and heated, to a distillation apparatus and collecting hydroxypivalaldehyde from the still residue.

7. The method according to claim 1, further comprising, after said distilling and said collecting, further distilling the still residue and collecting hydroxypivalaldehyde as a fraction.

8. The method according to claim 1, further comprising, after said distilling and said collecting, controlling a content of at least one compound selected from the group consisting of a compound represented by formula (2), a compound represented by formula (3), and a compound represented by formula (4):

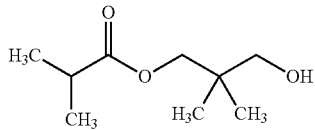
(2)

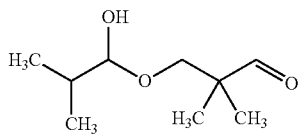
(3)

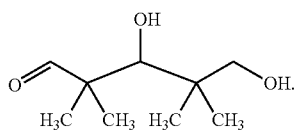
(4)

9. The method according to claim 1, further comprising, after said distilling and said collecting, controlling a content of a compound represented by formula (2):

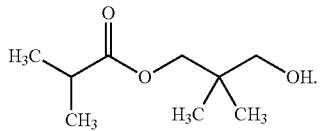
(2)

10. A compound, represented by formula (3) or formula (4):

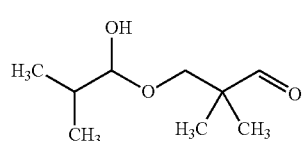
(3)

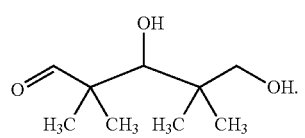
(4)

11. A method for producing a compound represented by formula (3), the method comprising reacting isobutyraldehyde with hydroxypivalaldehyde:

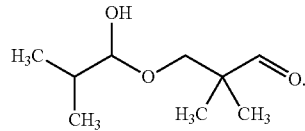
(3)

12. A method for producing a compound represented by formula (4), the method comprising reacting isobutyraldehyde with hydroxypivalaldehyde:

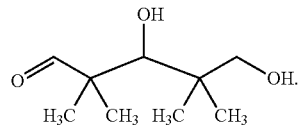
(4)

* * * * *